United States Patent

Malen et al.

[11] 3,960,891
[45] June 1, 1976

[54] THIOCHROMAN COMPOUNDS

[75] Inventors: Charles Malen, Fresnes; Michel Laubie, Vaucresson, both of France

[73] Assignee: Science-Union et Cie, France

[22] Filed: Mar. 31, 1971

[21] Appl. No.: 130,010

[30] Foreign Application Priority Data
Apr. 6, 1970  United Kingdom.............. 16118/70

[52] U.S. Cl. ........................... 260/327 TH; 424/275
[51] Int. Cl.² ....................................... C07D 335/06
[58] Field of Search ..................................... 260/327

[56] References Cited
UNITED STATES PATENTS

| | | | |
|---|---|---|---|
| 1,129,072 | 10/1968 | Turner | 260/345.2 |
| 3,328,417 | 6/1967 | McLoughlin et al. | 260/327 |
| 3,340,266 | 9/1967 | Howe et al. | 260/327 |
| 3,398,161 | 8/1968 | Turner | 260/330.5 |
| 3,705,167 | 12/1972 | Malen et al. | 269/327 |

OTHER PUBLICATIONS

Crowther et al., J. Med. Chem., vol. 15, pp. 260–266 (1972).

Howe et al. II, J. Med. Chem., vol. 13, pp. 169–176 Mar. 1970).

*Primary Examiner*—Harry I. Moatz
*Attorney, Agent, or Firm*—Gordon W. Hueschen

[57] ABSTRACT (3-amino-2-hydroxy propyloxy) thiochromans of the formula

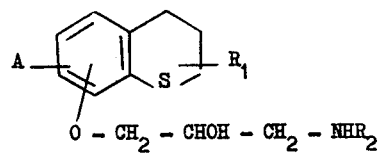

wherein A is hydrogen or halogen, $R_1$ is hydrogen or lower alkyl, and $R_2$ is lower alkyl or cyclo lower alkyl. These compounds possess cardiovascular properties and may be used as blockers of cardiac $\beta$ adrenergic receptors.

6 Claims, No Drawings

THIOCHROMAN COMPOUNDS

The present invention provides (3-amino-2-hydroxy propyloxy) thiochromans of the general formula I

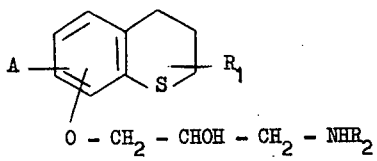

wherein:

A is selected from the group consisting of a hydrogen atom and halogen atoms;

$R_1$ is selected from the group consisting of a hydrogen atom and lower alkyl radicals containing from 1 to 5 carbon atoms inclusive; and $R_2$ is selected from the group consisting of linear and branched lower alkyl radicals containing 1 to 5 carbon atoms inclusive and cyclo lower alkyl radicals containing from 3 to 6 carbon atoms inclusive.

The compounds of the general formula I possess an asymetric carbon atom in 2-position of the propyloxy chain and, therefore, exist in the form of racemic compounds and optical dextrogyre and levogyre isomers, which are, consequently, included in the invention.

Furthermore, the compounds of the general formula I wherein $R_1$ represents a lower alkyl radical possess a second asymetric carbon atom and exist in the form of 4 optical isomers which are also included in the present invention.

The compounds of the general formula I are bases; they are mostly in the form of well-crystallized solids basic enough to form well-defined crystalline salts with mineral or organic acids. Among the acids used to form these salts, there may be mentioned in the mineral series, for example, hydrochloric, hydrobromic, sulfuric and phosphoric acids, and in the organic series, for example, acetic, propionic, maleic, fumaric, tartaric, citric, oxalic, benzoic and methanesulfonic acids. These salts are also included in the present invention.

The compounds of the general formula I are new and are prepared by reacting 1-chloro-2,3-epoxy propane,

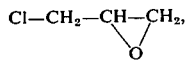

with a hydroxythiochroman of the general formula II

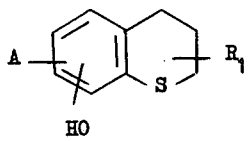

wherein A and $R_1$ have the above meanings, then condensing the so-obtained (2,3-epoxy propyloxy) thiochroman of the general formula III

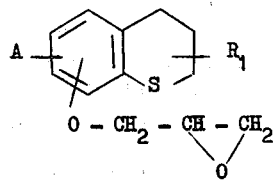

wherein A and $R_1$ have the above meanings, with a primary amine of the general formula IV

wherein $R_2$ has the above meanings.

The hydroxylated compounds of the general formula II, used as starting materials, have been described in our British Patent Application No 21 254/69 of 25th Apr. 1969. Some hydroxylated derivatives of the general formula II, used as starting materials, have been described in our British Patent Application No. 48,046/66 of 26 Oct. 1956, now British Pat. No. 1,158,473 published 16 July 1969. These hydroxylated derivatives which are new are described below in the Examples.

The compounds of the general formula I and their physiologically tolerable salts possess valuable pharmacological and therapeutic properties, especially cardiovascular properties, and may be used as blockers of cardiac β-adrenergic receptors.

The acute toxicity, studied in mice, as shown a $LD_{50}$ of 100 to 200 mg/kg when administered intraperitoneally.

The activity on β-adrenergic receptors was studied on the isolated auricle of the guinea-pig and on the anaesthetized or non-anaesthetized dog. It was observed that, in all the experimentations, the new compounds of the present invention inhibit the tachycardia and the hypertension provoked by isoprenaline. This activity appears when the new compounds are administered at a dose of 0,001 mg/kg I.V. on the anaesthetized dog. When administered at a dose of 0,010 mg/kg I.V., the new compounds decrease from 30 to 50 % the tachycardia induced by 1 mg/kg I.V. of isoprenaline, and the inhibition is complete when they are administered at a dose of 0,1 mg/kg. The action of the new compounds lasts very long and exceeds 7 hours. When administered at a dose of 0,2 to 0,5 mg/kg P.O. on the non-anaesthetized dog, the new compounds inhibit the tachycardia induced by 0,3 mg/kg of isoprenaline.

The compounds of the present invention, administered at a dose of 0,1 mg/kg I.V. on the anaesthetized dog, decrease the blood-pressor effect of noradrenaline, tyramine, angiotensin and the occlusion of the common carotids.

The above-mentioned properties allow the use of the new compounds in therapy, especially in the treatment of angina pectoris, hypertension and disorders of the cardiac rythm.

The present invention also provides pharmaceutical preparations containing a compound of the general formula I or a physiologically tolerable salt thereof, in admixture or conjunction with a suitable pharmaceutical carrier such as, for example, distilled-water, glucose, lactose, starch, talc, gum arabic, magnesium stearate, ethylcellulose and cocoa butter.

The pharmaceutical compositions may be in form of, for example, tablets, dragees, capsules, drinkable or injectable solutions or suppositories, and they may be administered by oral, rectal or parenteral route at doses of from 0,01 to 1 mg/kg.

A typical pharmaceutical preparation according to the present invention may have the following composition:

| | |
|---|---|
| dl 8-(2-hydroxy-3-tert-butylamino propyloxy) thiochroman hydrochloride | 5 mg |
| Lactose | 65 mg |
| Maize starch | 45 mg |
| Gum arabic | 3 mg |
| Talc | 6 mg |
| Magnesium stearate | 1 mg | for a tablet to be dragéefied.

The following examples illustrate the invention. The melting points were determined on a Kofler block (K) or on a Kofler heater plate under the microscope (M.K.).

EXAMPLE 1 dl 8-(3-isopropylamino-2-hydroxy propyloxy) thiochroman.

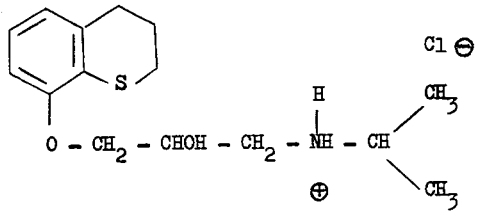

While agitating a methanolic sodium methylate solution prepared from 30.5 g (1.36 mols) of sodium and 540 ml of methanol, 191 g (1.36 mols) of redistilled orthomethoxythiophenol were added drop by drop.

Separately, a solution of 148 g (1.36 mols) of β-chloropropionic acid of 100% strength in 540 ml of methanol and 135 ml of water was accurately neutralized with 54.5 g (1.36 mols) of sodium hydroxide (100% pure) in 240 ml of water at 45°C, while preventing any heating up of the batch. The resulting solution of sodium β-chloropropionate was run during 15 minutes into the solution of sodium orthomethoxythiophenate containing sodium carbonate prepared as described above while agitating the whole well. The mixture was refluxed for 4 hours, and the methanol was then distilled off. The aqueous residue was diluted with 2 volumes of water, filtered and adjusted with hydrochloric acid to a pH value of 1 to 2.

β-(Orthomethoxyphenyl-mercapto)-propionic acid settled out in the form of an oil which crystallized by seeding. The mixture was triturated, suctioned off and washed with water, to yield after drying in a stove, 264.5 g of β-(orthomethoxyphenyl-mercapto)-propionic acid melting at 91°–93°C. Yield: 89%.

125 Grams (0.59 mol) of this crude acid were added portionwise to a solution of 200 ml of thionylchloride in 500 ml of anhydrous benzene. The mixture was refluxed for 2 hours and then evaporated to dryness. The residue was taken up with 1200 ml of anhydrous benzene and while stirring well, 300 g (2.25 mols) of aluminium chloride were added portionwise. Stirring was continued for 2 hours; the mixture was then left to stand for 48 hours and then hydrolyzed cautiously with water and hydrochloric acid. The expected phenolic compound settled out partially and dissolved partially in the benzene. The precipitate, which consisted of β-hydroxy-thiochroman-4-one in the crude state, was centrifuged and the benzene decanted. The benzenic part was extracted with 2 × 100 ml of 10% sodium hydroxide solution and then with water. The basic parts were combined with the centrifuged product, and while stirring the whole, 100 ml of 10% sodium hydroxide solution were added until all had dissolved. The mixture was filtered and reacidified to a pH value of 4 by means of hydrochloric acid, while preventing any heating up.

After centrifuging, washing with water and drying in a drying oven, there were obtained 63.2 g of 8-hydroxy-thiochroman-4-one, melting at 225°–232°C, in a yield of 60%.

40 Grams of 8-hydroxy-thiochroman-4-one were added portionwise to a mixture of 53.5 ml of hydrazine hydrate and 220 ml of ethanol. The reaction mixture was refluxed for 1 hour and then evaporated to dryness in vacuo. The residue was taken up in 250 ml of ethyleneglycol, and then 22.1 g of sodium hydroxide, were added in pellet form. The whole was heated to refluxing, while the water of reaction was distilled off as it is formed. The mixture was then heated for 4 hours at 200°C, allowed to cool and the bulk of glycol was expelled under vacuum. The residue was diluted with water and then acidified. The liberated phenol was extracted with chloroform. The chloroform extract was dried and evaporated and the residue distilled under vacuum, to yield 20.1 g of 8-hydroxy-thiochroman, boiling at 105°–110°C under 0.08 mm Hg pressure, in a yield of 55%. After recrystallization from cyclohexane it melted at 86°–88°C.

7 g (0.076 mol) of redistilled 1-chloro-2,3-epoxy propane were quickly added to a solution of 8.4 g (0.05 mol) of 8-hydroxy thiochroman, 2 g (0.05 mol) of sodium hydroxyde and 100 ml of water. The mixture was stirred for 5 hours, at 50° to 60°C. The precipitated oil was extracted with chloroform, washed with water, dried and evaporated. There were obtained 6.9 g of an oily residue mainly comprising 8-(2,3-epoxy propyloxy) thiochroman which were used in this form for the further reactions (yield: 62%).

A mixture of 6.9 g of crude 8-(2,3-epoxy propyloxy) thiochroman prepared as described above, 26 ml of isopropylamine and 53 ml of dry dioxan were refluxed for 20 hours. The reaction mixture was then evaporated to dryness, under vacuum. The residue was taken up with chloroform and diluted hydrochloric acid. The acid aqueous phase was made alkaline with an aqueous sodium hydroxide solution. There were obtained 4.6 g of dl 8-(3-isopropylamino-2-hydroxy propyloxy) thiochroman, melting (K) at 90° to 92°C, which recrystallized in cyclohexane, melted at 91 to 92°C. 3.9 g of this base were dissolved in 20 ml of ethanol and a solution of dry hydrochloric gas in ether was added.

After evaporation and recrystallization of the residue in ethanol, 3.5 g of dl 8-(3-isopropylamino-2-hydroxy propyloxy) thiochroman hydrochloride, melting (M.K.) at 188° to 192° C, were obtained.

EXAMPLES 2 – 11

The following compounds were prepared according to the method described in Example 1.

2. dl 8-(3-tert-butylamino-2-hydroxy propyloxy) thiochroman, M.P. (M.K.) 70° to 72°C (heptane), M.P. (M.K.) of its hydrochloride 180° to 183° C (acetonitrile), starting from 8-(2,3-epoxy propyloxy) thiochroman and tert-butylamine.

3. dl 8-(3-sec-butylamino-2-hydroxy propyloxy) thichroman, M.P. (M.K.) 80° to 82° C (cyclohexane), M.P. (M.K.) of its hydrochloride 138° to 140° C (acetonitrile), starting from 8-(2,3-epoxy propyloxy) thiochroman and sec-butylamine.

4. dl 8-(3-cyclopropylamino-2-hydroxy propyloxy) thiochroman, M.P. (M.K.) 76° to 78° C (cyclohexane), M.P. (M.K.) of its hydrochloride 170° to 173° C (acetonitrile/ethanol), starting from 8-(2,3-epoxy propyloxy) thiochroman and cyclopropylamine.

5. dl 8-(3-isopropylamino-2-hydroxy propyloxy)-2-methyl thiochroman, M.P. (M.K.) 102° to 104° C (cyclohexane), M.P. (M.K.) of its hydrochloride 149° to 152° C (acetonitrile), starting from 8-(2,3-epoxy propyloxy)-2-methyl thiochroman and isopropylamine; 8-(2,3-epoxy propyloxy)-2-methyl thiochroman was itself prepared starting from 1-chloro-2,3-epoxy propane and 8-hydroxy-2-methyl thiochroman.

6. dl 8-(3-isopropylamino-2-hydroxy propyloxy)-3-methyl thiochroman, M.P. (M.K.) 95° to 97° C (cyclohexane/benzene), M.P. (M.K.) of its hydrochloride 165° to 167° C (ethanol), starting from 8-(2,3-epoxy propyloxy)-3-methyl thiochroman and isopropylamine; 8-(2,3-epoxy propyloxy)-3-methyl thiochroman was itself prepared starting from 1-chloro-2,3-epoxy propane and 8-hydroxy-3-methyl thiochroman.

7. dl 6-(3-isopropylamino-2-hydroxy propyloxy) thiochroman, M.P. (M.K.) 90° to 92° C (cyclohexane), M.P. (M.K.) of its hydrochloride 159° to 161° C (acetonitrile), starting from 6-(2,3-epoxy propyloxy) thiochroman and isopropylamine; 6-(2,3-epoxy propyloxy) thiochroman was itself prepared starting from 1-chloro-2,3-epoxy propane and 6-hydroxy thiochroman.

8. dl 6-(3-isopropylamine-2-hydroxy propyloxy)-3-propyl thiochroman, starting from 6-(2,3-epoxy propyloxy)-3-propyl thiochroman and isopropylamine; 6-(2,3-epoxy propyloxy)-3-propyl thiochroman was itself prepared starting from 1-chloro-2,3-epoxy propane and 6-hydroxy-3-propyl thiochroman.

9. dl 7-(3-isopropylamino-2-hydroxy propyloxy)-2-methyl thiochroman, starting from 7-(2,3-epoxy propyloxy)-2-methyl thiochroman and isopropylamine; 7-(2,3-epoxy propyloxy)-2-methyl thiochroman was itself prepared starting from 1-chloro-2,3-epoxy propane and 7-hydroxy-2-methyl thiochroman.

10. dl 8-(3-tert-butylamino-2-hydroxy propyloxy)-6-chloro thiochroman, starting from 8-(2,3-epoxy propyloxy)-6-chloro thiochroman and tert-butylamine; 8-(2,3-epoxy propyloxy)-6-chloro thiochroman was itself prepared starting from 1-chloro-2,3-epoxy propane and 8-hydroxy-6-chloro thiochroman.

11. dl 8-(3-isopropylamino-2-hydroxy propyloxy)-7-fluoro thiochroman, starting from 8-(2,3-epoxy propyloxy)-7-fluoro thiochroman and isopropylamine; 8-(2,3-epoxy propyloxy)-7-fluoro thiochroman was itself prepared from 1-chloro-2,3-epoxy propane and 8-hydroxy-7-fluoro thiochroman.

What we claim is:

1. A compound selected from the group consisting of:
  a. (3-amino-2-hydroxy propyloxy) thiochromans of the formula

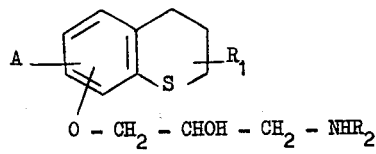

$O - CH_2 - CHOH - CH_2 - NHR_2$ wherein:
  A is selected from the group consisting of hydrogen and halogen;
  $R_1$ is selected from the group consisting of hydrogen and lower alkyl containing from 1 to 5 carbon atoms inclusive; and
  $R_2$ is selected from the group consisting of linear and branched lower alkyl containing from 1 to 5 carbon atoms inclusive and cyclo lower alkyl containing from 3 to 6 carbon atoms inclusive; and having the (3-amino-2-hydroxy propyloxy) group bonded to the thiochroman in the 6,7, or 8 position and
  b. Physiologically tolerable acid addition salts thereof.

2. A compound of claim 1 which is dl 8-(3-tert-butylamino-2-hydroxy propyloxy) thiochroman.

3. A compound of claim 1 which is dl 8-(3-cyclopropylamino-2-hydroxy propyloxy) thiochroman.

4. A compound of claim 1 which is dl 8-(3-isopropylamino-2-hydroxy propyloxy)-2-methyl thiochroman.

5. A compound of claim 1 which is dl 6-(3-isopropylamine-2-hydroxy propyloxy) thiochroman.

6. A compound of claim 1 wherein the (3-amino-2-hydroxy propyloxy) group is bonded to the thiochroman in the 8-position, and physiologicaly tolerable acid addition salts thereof.

* * * * *